(12) United States Patent
Irvine et al.

(10) Patent No.: US 6,300,056 B1
(45) Date of Patent: Oct. 9, 2001

(54) HIV PROBES FOR USE IN SOLUTION PHASE SANDWICH HYBRIDIZATION ASSAYS

(75) Inventors: Bruce D. Irvine, Concord; Janice A. Kolberg, Hercules; Michael S. Urdea, Alamo, all of CA (US)

(73) Assignee: Chiron Corporation, Emeryville, CA (US)

(*) Notice: Subject to any disclaimer, the term of this patent is extended or adjusted under 35 U.S.C. 154(b) by 0 days.

(21) Appl. No.: 08/169,715

(22) Filed: Dec. 17, 1993

Related U.S. Application Data

(63) Continuation of application No. 07/813,583, filed on Dec. 23, 1991, now abandoned.

(51) Int. Cl.[7] ............................. C12Q 1/68; C07H 21/04
(52) U.S. Cl. ............................. 435/5; 435/6; 435/810; 536/23.1; 536/24.32; 536/24.33
(58) Field of Search .................. 435/5, 6, 810; 536/23.72, 24.32, 24.332, 23.1; 935/78.8

(56) References Cited

U.S. PATENT DOCUMENTS

| | | | |
|---|---|---|---|
| 4,868,105 | 9/1989 | Urdea et al. | 435/6 |
| 5,008,182 * | 4/1991 | Sninsky | 435/5 |
| 5,030,557 | 7/1991 | Hogan et al. | 435/6 |
| 5,124,246 * | 6/1992 | Urdea et al. | 435/6 |

FOREIGN PATENT DOCUMENTS

| | | | |
|---|---|---|---|
| 2002076 | 2/1989 | (CA) | |
| 0225807 | 6/1987 | (EP) | |
| 0229701 | 7/1987 | (EP) | |
| 0272098 | 6/1988 | (EP) | |
| 0326395 | 2/1989 | (EP) | |
| 0318245 * | 5/1989 | (EP) | 435/6 |
| 0370694 | 5/1990 | (EP) | |
| 0 403 333 | 12/1990 | (EP) | |
| WO 87/03621 | 6/1987 | (WO) | |
| WO 87/07906 | 12/1987 | (WO) | |
| WO 87/07912 | 12/1987 | (WO) | |
| WO 88/01302 | 2/1988 | (WO) | |
| WO 88/05440 | 7/1988 | (WO) | |
| 8903891 * | 5/1989 | (WO) | 435/6 |
| WO 89/10979 | 11/1989 | (WO) | |
| WO 90/08840 | 8/1990 | (WO) | |
| WO 91/10746 | 7/1991 | (WO) | |
| WO 91/19812 | 12/1991 | (WO) | |
| WO 92/16219 | 10/1992 | (WO) | |

OTHER PUBLICATIONS

Ratner et al. Nature (1985) 313:277–284.*
Grankvist et al AIDS (1991) 5:275–578.*
Albert et al J. Clin Microbiol (Jul. 1990) 28:1560–1564.*
Perrin et al Blood (1990) 76:641–645.*
Conway et al J. Acquired Immune Defic Syndromes (1990) 3:1059–1064.*
Louis et al., "Chemical synthesis and expression of the HIV-1 protease gene in *E. Coli*" *Biochem. & Biophys. Res. Comm.* (1989) 159:87–94.
Spector et al., *Clin. Chem.* (1989) 35(8):1581–1587.
Kellog et al., *analytical Biochem.* (1990) 189:202–208.
Lomell et al., *Clin. Chem.* (1989) 35/5:1826–1831.
Coutlee et al., *Analytical Biochem.* (1989) 181:96–105.
Thompson et al., *Clin. Chem.* (1989) 35/9:1878–1881.
Gillespie et al., *Mol. Cell. Probes* (1989) 3:73–86.
Keller et al., *Analytical Biochem.* (1989) 177:27–32.
Viscidi et al., *J. Clin. Micro.* (1989) 27(1):120–125.
Buchbinder et al., *J. Virol. Meth.* (1988) 21:191–197.
Kumar et al., *Aids Res. Human Retroviruses* (1989) 5(3):345–354.
Ou et al., *Science* (1988) 239(4837):295–297.
de la Maza, L.M., et al., Eds., *Medical Virology* (1985) Lawrence Erlbaum Associates, Publishers, Hillsdale, New Jersey, pp. 31–64.

* cited by examiner

Primary Examiner—Carla J. Myers
(74) Attorney, Agent, or Firm—Thomas E. Ciotti; Alisa A. Harbin; Robert P. Blackburn

(57) ABSTRACT

Novel DNA probe sequences for detection of HIV in a sample in a solution phase sandwich hybridization assay are described. Amplified nucleic acid hybridization assays using the probes are exemplified.

20 Claims, No Drawings

HIV PROBES FOR USE IN SOLUTION PHASE SANDWICH HYBRIDIZATION ASSAYS

This application is a continuation, of application Ser. No. 07/813,583 filed Dec. 23. 1991, now abandoned.

TECHNICAL FIELD

This invention is in the field of nucleic acid hybridization assays. More specifically, it relates to novel nucleic acid probes for detecting Human Immunodeficiency Virus (HIV).

BACKGROUND ART

The etiological agent of AIDS and ARC has variously been termed LAV, HTLV-III, ARV, and HIV. Hereinafter it will be referred to as HIV. Detection of the RNA or DNA of this virus is possible through a variety of probe sequences and hybridization formats.

PCT WO 88/01302, filed Aug. 11, 1987, discloses thirteen HIV oligonucleotides for use as probes in detecting HIV DNA or RNA. PCT WO 87/07906, filed Jun. 22, 1987, discloses variants of HIV viruses and the use of their DNA to diagnoses AIDS. EP 0 326 395 A2, filed Jan. 27, 1989, discloses an HIV DNA probe spanning nucleotides 2438–2457 for detecting sequences associated with multiple sclerosis.

The advent of the polymerase chain reaction has stimulated a range of assays using probes mainly from regions of the pol and gag genes. Spector et al. (*Clin. Chem.* 35/8:1581–1587, 1989) and Kellog et al. (*Analytical Biochem* 189:202–208, 1990) disclose a quantitative assay for HIV proviral DNA using polymerase chain reaction using a primer from the HIV gag gene. Lomell et al. (*Clin. Chem.* 35/9:1826–1831) disclose an amplifiable RNA probe complementary to a conserved region of the HIV pol gene mRNA. Coutlee et al. (Anal. Biochem. 181:96–105, 1989) disclose immunodetection of HIV DNA using the polymerase chain reaction with a set of primers complementary to sequences from the HIV pol and gag genes. EP 0 272 098, filed Dec. 15, 1987, discloses PCR amplification and detection of HIV RNA sequences using oligonucleotide probes spanning nucleotides 8538–8547 and 8658–8677. EP 0 229 701, filed Jan. 9, 1987 discloses detection of HIV by amplification of DNA from the HIV gag region. PCT WO 89/10979 discloses a nucleic acid probe assay combining amplification and solution hybridization using capture and reporter probes followed by immobilization on a solid support. A region within the gag p 17 region of HIV was amplified with this technique.

An alternative strategy is termed "reversible target capture." For example, Thompson et al. (*Clin. Chem.* 35/9:178–1881, 1989) disclose "reversible target capture" of HIV RNA, wherein a commercially available dA-tailed synthetic oligonucleotide provided selective purification of the analyte nucleic acid, and a labeled antisense RNA probe complementary to the HIV pol gene provided signal. Gillespie et al. (*Molecular and Cellular Probes* 3:73–86, 1989) discloses probes for reversible target capture of HIV RNA, wherein the probes are complementary to nucleotides 2094–4682 of the HIV pol gene.

Kumar et al. disclose a "probe shift" assay for HIV DNA, using DNA sequences complementary to the HIV gag and pol genes. The probe shift assay depends on the hybridization of a labeled oligonucleotide to a PCR-amplified segment in solution. The hemiduplex thereformed is detected following fractionation on nondenaturing gels.

Keller et al. (*Anal. Biochem.* 177:27–32, 1989) disclose a microtiter-based sandwich assay to detect HIV DNA spanning the Pst I site of the gag coding region.

Viscidi et al. (*J. Clin. Micro.* 27:120–125, 1989) disclose a hybridization assay for HIV RNA using a solid phase anti-biotin antibody and an enzyme-labeled monoclonal antibody specific for DNA-RNA hybrids, wherein the probe spanned nearly all of the polymerase gene and the 3' end of the gag gene.

European Patent Application (EPA) 89311862, filed Nov. 16, 1989 discloses a diagnostic kit and method using a solid capture means for detecting nucleic acid, and describes the use of DNA sequences complementary to the HIV gag gene to detect HIV DNA.

Commonly owned U.S. Pat. No. 4,868,105 issued Sep. 19, 1989, describes a solution phase nucleic acid sandwich hybridization assay in which analyte nucleic acid is first hybridized in solution to a labeling probe set and to a capturing probe set in a first vessel. The probe-analyte complex is then transferred to a second vessel that contains a solid-phase-immobilized probe that is complementary to a segment of the capturing probes. The segments hybridize to the immobilized probe, thus removing the complex from solution. Having the analyte in the form of an immobilized complex facilitates subsequent separation steps in the assay. Ultimately, single stranded segments of the labeling probe set are hybridized to labeled probes, thus permitting the analyte-containing complex to be detected via a signal generated directly or indirectly from the label.

Commonly owned European Patent Application (EPA) 883096976 discloses a variation in the assay described in U.S. Pat. No. 4,868,105 in which the signal generated by the labeled probes is amplified. The amplification involves the use of nucleic acid multimers. These multimers are branched polynucleotides that are constructed to have a segment that hybridizes specifically to the analyte nucleic acid or to a nucleic acid (branched or linear) that is bound to the analyte and iterations of a second segment that hybridize specifically to the labeled probe. In the assay employing the multimer, the initial steps of hybridizing the analyte to label or amplifier probe sets and capturing probe sets in a first vessel and transferring the complex to another vessel containing immobilized nucleic acid that will hybridize to a segment of the capturing probes are followed. The multimer is then hybridized to the immobilized complex and the labeled probes in turn hybridized to the second segment iterations on the multimer. Since the multimers provide a large number of sites for label probe attachment, the signal is amplified. Amplifier and capture probe sequences are disclosed for Hepatitis B virus, *Neisseria gonorrhoeae*, penicillin and tetracycline resistance in *N. gonorrhoeae*, and *Chlamydia trachomatis*.

Commonly owned copending application Ser. No. 558, 897, filed Jul. 27, 1990, describes the preparation of large comb-type branched polynucleotide multimers for use in the above-described solution phase assay. The combs provide greater signal enhancement in the assays than the smaller multimers.

U.S. Pat. No. 5,030,557, issued Jul. 9, 1991, discloses a "helper" oligonucleotide selected to bind to the analyte nucleic acid and impose a different secondary and tertiary structure on the target to facilitate the binding of the probe to the target.

Disclosure of the Invention

One aspect of the invention is a synthetic oligonucleotide useful as an amplifier probe in a sandwich hybridization assay for HIV comprising a first segment having a nucleotide sequence substantially complementary to a segment of HIV nucleic acid; and a second segment having a nucleotide sequence substantially complementary to an oligonucleotide unit of a nucleic acid multimer.

Another aspect of the invention is a synthetic oligonucleotide useful as a capture probe in a sandwich hybridization assay for HIV comprising a first segment having a nucleotide sequence substantially complementary to a segment of HIV nucleic acid; and a second segment having a nucleotide sequence substantially complementary to an oligonucleotide bound to a solid phase.

Another aspect of the invention is a spacer oligonucleotide for use in sandwich hybridizations to detect HIV.

Another aspect of the invention is a solution sandwich hybridization assay for detecting the presence of HIV in a sample, comprising (a) contacting the sample under hybridizing conditions with an excess of (i) an amplifier probe oligonucleotide comprising a first segment having a nucleotide sequence substantially complementary to a segment of HIV nucleic acid and a second segment having a nucleotide sequence substantially complementary to an oligonucleotide unit of a nucleic acid multimer and (ii) a capture probe oligonucleotide comprising a first segment having a nucleotide sequence that is substantially complementary to a segment of HIV nucleic acid and a second segment that is substantially complementary to an Ligonucleotide bound to a solid phase;

(b) contacting the product of step (a) under hybridizing conditions with said oligonucleotide bound to the solid phase;

(c) thereafter separating materials not bound to the solid phase;

(d) contacting the bound product of step (c) under hybridization conditions with the nucleic acid multimer, said multimer comprising at least one oligonucleotide unit that is substantially complementary to the second segment of the amplifier probe polynucleotide and a multiplicity of second oligonucleotide units that are substantially complementary to a labeled oligonucleotide;

(e) removing unbound multimer;

(f) contacting under hybridizing conditions the solid phase complex product of step (e) with the labeled oligonucleotide;

(g) removing unbound labeled oligonucleotide; and (h) detecting the presence of label in the solid phase complex product of step (g).

Another aspect of the invention is a kit for the detection of HIV in a sample comprising in combination (i) a set of amplifier probe oligonucleotides wherein the amplifier probe oligonucleotide comprises a first segment having a nucleotide sequence substantially complementary to a segment of HIV nucleic acid and a second segment having a nucleotide sequence substantially complementary to an oligonucleotide unit of a nucleic acid multimer;

(ii) a set of capture probe oligonucleotides wherein the capture probe oligonucleotide comprises a first segment having a nucleotide sequence that is substantially complementary to a segment of HIV nucleic acid and a second segment that is substantially complementary to an oligonucleotide bound to a solid phase;

(iii) a nucleic acid multimer, said multimer comprising at least one oligonucleotide unit that is substantially complementary to the second segment of the amplifier probe polynucleotide and a multiplicity of second oligonucleotide units that are substantially complementary to a labeled oligonucleotide; and (iv) a labeled oligonucleotide.

Modes for Carrying out the Invention Definitions

"Solution phase nucleic acid hybridization assay" intends the assay techniques described and claimed in commonly owned U.S. Pat. No. 4,868,105, EPA 883096976, and U.S. Ser. No. 558,897.

A "modified nucleotide" intends a nucleotide monomer that may be stably incorporated into a polynucleotide and which has an additional functional group. Preferably, the modified nucleotide is a 5' cytidine in which the $N^4$-position is modified to provide a functional hydroxy group.

An "amplifier multimer" intends a branched polynucleotide that is capable of hybridizing simultaneously directLy or indirectly to analyte nucleic acid and to a multiplicity of polynucleotide iterations (i.e, either iterations of another multimer or iterations of a labeled probe). The branching in the multimers is effected through covalent bonds and the multimers are composed of two types of oligonucleotide units that are capable of hybridizing, respectively, to analyte nucleic acid or nucleic acid hybridized to analyte nucleic acid and to a multiplicity of labeled probes. The composition and preparation of such multimers are described in EPA 883096976 and U.S. Ser. No. 558,897 filed Jul. 27, 1990, the disclosures of which are incorporated herein by reference.

A "spacer oligonucleotide" is intended as an oligonucleotide which binds to analyte RNA but does not contain any sequences for attachment to a solid phase nor any means for detection by an amplifier probe.

The term "amplifier probe" is intended as a branched or linear polynucleotide that is constructed to have a segment that hybridizes specifically to the analyte nucleic acid and a segment or iterations of a segment that hybridize specifically to an amplifier multimer.

The term "capture probe" is intended as an oligonucleotide having a segment substantially complementary to a nucleotide sequence of the analyte nucleic acid and a segment that is substantially complementary to a nucleotide sequence of a solid-phase-immobilized probe.

"Large" as used herein to describe the comb-type branched polynucleotides of the invention intends a molecule having at least about 15 branch sites and at least about 20 iterations of the labeled probe binding sequence.

"Comb-type" as used herein to describe the structure of the branched polynucleotides of the invention intends a polynucleotide having a linear backbone with a multiplicity of sidechains extending from the backbone.

A "cleavable linker molecule" intends a molecule that may be stably incorporated into a polynucleotide chain and which includes a covalent bond that may be broken or cleaved by chemical treatment or physical treatment such as by irradiation.

All nucleic acid sequences disclosed herein are written in a 5' to 3' direction. Nucleotides are designated according to the nucleotide symbols recommended by the IUPAC-IUB Biochemical Nomenclature Commission.

Solution Phase Hybridization Assay

The general protocol for the solution phase sandwich hybridizations is as follows. The analyte nucleic acid is placed in a microtiter well with an excess of two single-stranded nucleic acid probe sets: (1) a set of capture probes, each having a first binding sequence substantially complementary to the analyte and a second binding sequence that is substantially complementary to nucleic acid bound to a solid support, for example, the well surface or a bead, and (2) a set of amplifier probes (branched or linear), each having a first binding sequence that is capable of specific binding to the analyte and a second binding sequence that is capable of specific binding to a segment of the multimer. The resulting product is a three component nucleic acid complex of the two probes hybridized to the analyte by their first: binding sequences. The second binding sequences of the probes remain as single-stranded segments as they are not substantially complementary to the analyte. This complex hybridizes to the immobilized probe on the solid surface via the second binding sequence of the capture probe. The resulting product comprises the domplex bound to the solid surface via the duplex formed by the oligonucleotide bound to the solid surface and the second binding sequence of the capture probe. Unbound materials are then removed from the surface such as by washing.

The amplification multimer is then added to the bound complex under hybridization conditions to permit the multimer to hybridize to the available second binding sequence (s) of the amplifier probe of the complex. The resulting complex is then separated from any unbound multimer by washing. The labeled oligonucleotide is then added under conditions which permit it to hybridize to the substantially complementary oligonucleotide units of the multimer. The resulting immobilized labeled nucleic acid complex is then washed to remove unbound labeled oligonucleotide, and read.

The analyte nucleic acids may be from a variety of sources, e.g., biological fluids or solids, and may be prepared for the hybridization analysis by a variety of means, e.g., proteinase K/SDS, chaotropic salts, etc. Also, it may be of advantage to decrease the average size of the analyte nucleic acids by enzymatic, physical or chemical means, e.g., restriction enzymes, sonication, chemical degradation (e.g., metal ions), etc. The fragments may be as small as 0.1 kb, usually being at least about 0.5 kb and may be 1 kb or higher. The analyte sequence is provided in single-stranded form for analysis. Where the sequence is naturally present in single-stranded form, denaturation will not be required. However, where the sequence may be present in double-stranded form, the sequence should be denatured. Denaturation can be carried out by various techniques, such as alkali, generally from about 0.05 to 0.2 M hydroxide, formamide, salts, heat, enzymes, or combinations thereof.

The first binding sequences of the capture probe and amplifier probe that are substantially complementary to the analyte sequence will each be of at least 15 nucleotides, usually at least 25 nucleotides, and not more than about 5 kb, usually not more than about 1 kb, preferably not more than about 100 nucleotides. They will typically be approximately 30 nucleotides. They will normally be chosen to bind to different sequences of the analyte. The first binding sequences may be selected based on a variety of considerations. Depending upon the nature of the analyte, one may be interested in a consensus sequence, a sequence associated with polymorphisms, a particular phenotype or genotype, a particular strain, or the like.

The number of different amplifier and capture probes used influences the sensitivity of the assay, because the more probe sequences used, the greater the signal provided by the assay system. Furthermore, the use of more probe sequences allows the use of more stringent hybridization conditions, thereby reducing the incidence of false positive results. Thus, the number of probes in a set will be at least one capture probe and at least one amplifier probe, more preferably two capture and two amplifier probes, and most preferably 5–100 capture probes and 5–100 amplifier probes. Oligonucleotide probe sequences for HIV were designed by aligning the DNA sequences of 18 HIV strains from GenBank. Regions of greatest homology within the pol gene were selected as capture probes, while regions of lesser homology were selected as amplifier probes. Very heterogeneous regions were selected as spacer probes. Thus, as more strains of HIV are identified and sequenced, additional probes may be designed or the presently preferred set of probes modified by aligning the sequence of the new strain or isolate with the 18 strains used above and similarly identifying regions of greatest homology and lesser homology.

Spacer oligonucleotides were designed to be added to the hybridization cocktail to protect RNA from possible degradation. Capture probe sequences and label probe sequences were designed so that capture probe sequences were interspersed with label probe sequences, or so that capture probe sequences were clustered together with respect to label probe sequences.

The presently preferred set of probes and their capture or amplifier regions which hybridize specifically to HIV nucleic acid are listed in Example 2.

The second binding sequences of the capture probe and amplifier probe are selected to be substantially complementary, respectively, to the oligonucleotide bound to the solid surface and to a segment of the multimer and so as to not be encountered by endogenous sequences in the sample/analyte. The second binding sequence may be contiguous to the first binding sequence or be spaced therefrom by an intermediate noncomplementary sequence. The probes may include other noncomplementary sequences if desired. These noncomplementary sequences must not hinder the binding of the binding sequences or cause nonspecific binding to occur.

The capture probe and amplifier probe may be prepared by oligonucleotide synthesis procedures or by cloning, preferably the former.

It will be appreciated that the binding sequences need not have perfect complementarity to provide homoduplexes. In many situations, heteroduplexes will suffice where fewer than about 10% of the bases are mismatches, ignoring loops of five or more nucleotides. Accordingly, as used herein the term "complementary" intends exact complementarity wherein each base within the binding region corresponds exactly, and "substantially complementary" intends 90% or greater homology.

The labeled oligonucleotide will include a sequence substantially complementary to the repeated oligonucleotide units of the multimer. The labeled oligonucleotide will include one or more molecules ("labels"), which directly or indirectly provide a detectable signal. The labels may be bound to individual members of the substantially complementary sequence or may be present as a terminal member or terminal tail having a plurality of labels. Various means for providing labels bound to the oligonucleotide sequences have been reported in the literature. See, for example, Leary et al., *Proc. Natl. Acad. Sci. USA* (1983) 80:4045; Renz and Kurz, *Nucl. Acids Res.* (1984) 12:3435; Richardson and Gumport, *Nucl. Acids Res.* (1983) 11:6167; Smith et al., *Nucl. Acids. Res.* (1985) 13:2399; Meinkoth and Wahl, *Anal.*

*Biochem.* (1984) 138:267. The labels may be bound either covalently or non-covalently to the substantially complementary sequence. Labels which may be employed include radionuclides, fluorescers, chemiluminescers, dyes, enzymes, enzyme substrates, enzyme cofactors, enzyme inhibitors, enzyme subunits, metal ions, and the like. Illustrative specific labels include fluorescein, rhodamine, Texas red, phycoerythrin, umbelliferone, luminol, NADPH, $\alpha$-$\beta$-galactosidase, horseradish peroxidase, alkaline phosphatase, etc.

The ratio of capture probe and amplifier probe to anticipated moles of analyte will each be at least stoichiometric and preferably in excess. This ratio is preferably at least about 1.5:1, and more preferably at least 2:1. It will normally be in the range of 2:1 to 10,000:1. Concentrations of each of the probes will generally range from about $10^{-5}$ to $10^{-9}$ M, with sample nucleic acid concentrations varying from $10^{-21}$ to $10^{-12}$ M. The hybridization steps of the assay will generally take from about 10 minutes to 20 hours, frequently being completed in about 1 hour. Hybridization can be carried out at a mildly elevated temperature, generally in the range from about 20° C. to 80° C., more usually from about 35° C. to 70° C., particularly 65° C.

The hybridization reactions are usually done in an aqueous medium, particularly a buffered aqueous medium, which may include various additives. Additives which may be employed include low concentrations of detergent (0.1 to 1%), salts, e.g., sodium citrate (0.017 to 0.17 M), Ficoll, polyvinylpyrrolidone, carrier nucleic acids, carrier proteins, etc. Nonaqueous solvents may be added to the aqueous medium, such as dimethylformamide, dimethylsulfoxide, alcohols, and formamide. These other solvents are generally present in amounts ranging from 2 to 50%.

The stringency of the hybridization medium may be controlled by temperature, salt concentration, solvent system, and the like. Thus, depending upon the length and nature of the sequence of interest, the stringency will be varied.

Depending upon the nature of the label, various techniques can be employed for detecting the presence of the label. For fluorescers, a large number of different fluorometers are available. For chemiluminescers, luminometers or films are available. With enzymes, a fluorescent, chemiluminescent, or colored product can be provided and determined fluorometrically, luminometrically, spectrophotometrically or visually. The various labels which have been employed in immunoassays and the techniques applicable to immunoassays can be employed with the subject assays.

The following examples further illustrate the invention. These examples are not intended to limit the invention in any manner.

EXAMPLES

Example I

Synthesis of Comb-type Branched Polynucleotide

This example illustrates the synthesis of a comb-type branched polynucleotide having 15 branch sites and sidechain extensions having three labeled probe binding sites. This polynucleotide was designed to be used in a solution phase hybridization as described in EPA 883096976.

All chemical syntheses of oligonucleotides were performed on an automatic DNA synthesizer (Applied Biosystems, Inc., (ABI) model 380 B). Phosphoramidite chemistry of the beta cyanoethyl type was used including 5'-phosphorylation which employed PHOSTEL™ reagent (DMT—O—$CH_2CH_2$—($SO_2$)—$CH_2CH_2$—O—P(—N$(iPr)_2$) (—O—$CH_2CH_2CN$) wherein DMT is dimethoxytrityl and iPr is isopropyl) reagent (ABN). Standard ABI protocols were used except as indicated. Where it is indicated that a multiple of a cycle was used (e.g., 1.2 cycle), the multiple of the standard amount of amidite recommended by ABI was employed in the specified cycle. Appended hereto are the programs for carrying out cycles 1.2 and 6.4 as run on the Applied Biosystems Model 380 B DNA Synthesizer.

A comb body of the following structure was first prepared:

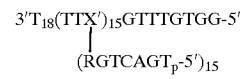

wherein X' is a branching monomer, and R is a periodate cleavable linker.

The portion of the comb body through the 15 (TTX') repeats is first synthesized using 33.8 mg aminopropyl-derivatized thymidine controlled pore glass (CPG) (2000 Å, 7.4 micromoles thymidine per gram support) with a 1.2 cycle protocol. The branching site nucleotide was of the formula:

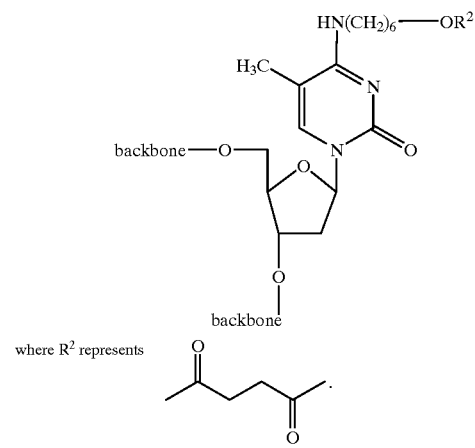

For synthesis of the comb body (not including sidechains), the concentration of beta cyanoethylphosphoramidite monomers was 0.1 M for A, C, G and T, 0.15 M for the branching site monomer E, and 0.2 M for PHOSTEL™ reagent (DMT—O—$CH_2CH_2$—($SO_2$)—$CH_2CH_2$—O—P(—$N(iPr)_2$) (—O—$CH_2CH_2CN$) wherein DMT is dimethoxytrityl and iPr is isopropyl reagent. Detritylation was done with 3% trichloroacetic acid in methylene chloride using stepped flowthrough for the duration of the deprotection. At the conclusion the 5' DMT was replaced with an acetyl group.

Cleavable linker R and six base sidechain extensions of the formula 3'-RGTCAGTp (SEQ ID NO:1) were synthesized at each branching monomer site as follows. The base protecting group removal ($R^2$ in the formula above) was performed manually while retaining the CPG support in the same column used for synthesizing the comb body. In the case of R²=levulinyl, a solution of 0.5 M hydrazine hydrate in pyridine/glacial acetic acid (1:1 v/v) was introduced and kept in contact with the CPG support for 90 min with renewal of the liquid every 15 min, followed by extensive washing with pyridine/glacial acetic acid (1:1 v/v) and then by acetonitrile. After the deprotection the cleavable linker R and six base sidechain extensions were added using a 6.4 cycle.

In these syntheses the concentration of phosphoramidites was 0.1 M (except 0.2 M R and PHOSTEL™ reagent (DMT—O—CH$_2$CH$_2$—(SO$_2$)—CH$_2$CH$_2$—O—P(—N(iPr)$_2$) (—O—CH$_2$CH$_2$CN) wherein DMT is dimethoxytrityl and iPr is isopropyl reagent; R was 2-(4-(4-(2-Dimethoxytrityloxy)ethyl-)phenoxy 2,3-di(benzoyloxy)-butyloxy)phenyl)ethyl-2-cyanoethyl-N,N-diisopropylphosphoramidite).

Detritylation is effected with a solution of 3% trichloroacetic acid in methylene chloride using continuous flowthrough, followed by a rinse solution of toluene/chloromethane (1:1 v/v). Branched polynucleotide chains were removed from the solid supports automatically in the 380B using the cycle "CE NH$_3$." The ammonium hydroxide solution was collected in 4 ml screw-capped Wheaton vials and heated at 60° C. for 12 hr to remove all base-protecting groups. After cooling to room temperature the solvent was removed in a Speed-Vac evaporator and the residue dissolved in 100 μl water.

3' backbone extensions (segment A), sidechain extensions and ligation template/linkers of the following structures were also made using the automatic synthesizer:
3' Backbone
  extension 3'-TCCGTATCCTGGGCACAGAGGTGCp-5' (SEQ ID NO:2)
Sidechain
  extension 3'-GATGCG(TTCATGCTGTTGGTGTAG)$_3$-5' (SEQ ID NO:3)
Ligation template for
  linking 3'
  backbone
  extension 3'-AAAAAAAAAAGCACCTp-5' (SEQ ID NO:4)
Ligation template for linking sidechain
  extension 3'-CGCATCACTGAC-5' (SEQ ID NO:5)

The crude comb body was purified by a standard polyacrylamide gel (7% with 7 M urea and 1× TBE running buffer) method.

The 3' backbone extension and the sidechain extensions were ligated to the comb body as follows. The comb body (4 pmole/μl), 3' backbone extension (6.25 pmole/μl), sidechain extension (93.75 pmole/μl) and linking template (5 pmole/μl) were combined in 1 mM ATP/5 mM DTT/ 50 mM Tris-HCl, pH 8.0/10 mM MgCl$_2$/2 mM spermidine, with 0.5 units/μl T4 polynucleotide kinase. The mixture was incubated at 37° C. for 2 hr, then heated in a water bath to 95° C., and then cooled to below 35° C. for about 1 hr. 2 mM ATP, 10 mM DTT, 14% polyethylene glycol, and 0.21 units/μl T4 ligase were added, and the mixture incubated for 16–24 hr at 23° C. The DNA was precipitated in NaCl/iethanol, resuspended in water, and subjected to a second ligation as follows. The mixture was adjusted to 1 mM ATP, 5 mM DTT, 14% polyethylene glycol, 50 mM Tris-HC1, pH 7.5, 10 mM MgCl$_2$, 2 mM spermidine, 0.5 units/μl T4 polynucleotide kinase, and 0.21 units/μl T4 ligase were added, and the mixture incubated at 23° C. for 16–24 hr. Ligation products were then purified by polyacrylamide gel electrophoresis.

After ligation and purification, a portion of the product was labeled with $^{32}$p and subjected to cleavage at the site of R achieved by oxidation with aqueous NaIO$_4$ for 1 hr. The sample was then analyzed by PAGE to determine the number of sidechain extensions incorporated by quantitating the radioactive label in the bands on the gel. The product was found to have a total of 45 labeled probe binding sites.

Example 2

Sandwich Hybridization Assay for HIV DNA using Multimer

This example illustrates the use of the invention in an HIV DNA assay.

A "15×3" amplified solution phase nucleic acid sandwich hybridization assay format was employed in this example. The "15×3" designation derives from the fact that the format employs two multimers: (1) an amplifier probe having a first segment (A) that binds to HIV nucleic acid and a second segment (B) that hybridizes to (2) an amplifier multimer having a first segment (B*) that hybridizes to the segment (B) and fifteen iterations of a segment (C), wherein segment C hybridizes to three labeled oligonucleotides.

The amplifier and capture probe HIV-specific segments, and their respective names as used in this assay were as follows.

HIV Amplifier Probes
HIV.104 (SEQ ID NO:5)
  TTCCTGGCAAAYYYATKTCTYCTAMTACTGTAT
HIV.105 (SEQ ID NO:6)
  CTCCAATTCCYCCTATCATTTTTGGYTTCCATY
HIV.106 (SEQ ID NO:7)
  KTATYTGATCRTAYTGTCYYACTTTGATAAAAC
HIV.108 (SEQ ID NO:8)
  GTTGACAGGYGTAGGTCCTACYAATAYTGTACC
HIV.110 (SEQ ID NO:9)
  YTCAATAGGRCTAATKGGRAAATTTAAAGTRCA
HIV.112 (SEQ ID NO:10)
  YTCTGTCAATGGCCATTGYTTRACYYTTGGGCC
HIV.113 (SEQ ID NO:11)
  TKTACAWATYTCTRYTAATGCTTTTATTTTYTC
HIV.114 (SEQ ID NO:12)
  AAYTYTTGAAATYTTYCCTTCCTTTTCCATHTC
HIV.115 (SEQ ID NO:13)
  AAATAYKGGAGTAATTRTATGGATTYTCAGGCCC
HIV.116 (SEQ ID NO:14)
  TCTCCAYTTRGTRCTGTCYTTTTTCTTTATRGC
HIV.117 (SEQ ID NO:15)
  TYTYYTATTAAGYTCYCTGAAATCTACTARTTT
HIV.120 (SEQ ID NO:16)
  TKTTYTAAARGGYTCYAAGATTTTTGTCATRCT
HIV.121 (SEQ ID NO:17)
  CATGTATTGATADATRAYYATKTCTGGATTTTG
HIV.122 (SEQ ID NO:18)
  TATYTCTAARTCAGAYCCTACATACAAATCATC
HIV.123 (SEQ ID NO:19)
  TCTYARYTCCTCTATTTTTGYTCTATGCTGYYC
HIV.125 (SEQ ID NO:20)
  AAGRAATGGRGGTTCTTTCTGATGYTTYTTRTC
HIV.128 (SEQ ID NO:21)
  TRGCTGCYCCATCTACATAGAAVGTTTCTGCWC
HIV.130 (SEQ ID NO:22)

GACAACYTTYTGTCTTCCAYTGTYAGTWASATA
HIV.132 (SEQ ID NO:23)
 YGAATCCTGYAAVGCTARRTDAATTGCTTGTAA
HIV.133 (SEQ ID NO:24)
 YTGTGARTCTGTYACTATRTTTACTTCTRRTCC
HIV.135 (SEQ ID NO:25)
 TATTATTTGAYTRACWAWCTCTGATTCACTYTK
HIV.136 (SEQ ID NO:26)
 CAGRTARACYTTTTCCTTTTTTATTARYTGYTC
HIV.137 (SEQ ID NO:27)
 TCCTCCAATYCCTTTRTGTGCTGGTACCCATGM
HIV.138 (SEQ ID NO:28)
 TCCHBBACTGACTAATYTATCTACTTGTTCATT
HIV.139 (SEQ ID NO:29)
 ATCTATTCCATYYAAAAATAGYAYYTTYCTGAT
HIV.141 (SEQ ID NO:30)
 GTGGYAGRTTAAARTCAYTAGCCATTGCTYTCC
HIV.142 (SEQ ID NO:31)
 CACAGCTRGCTACTATTTCYTTYGCTACYAYRG
HIV.144 (SEQ ID NO:32)
 RYTGCCATATYCCKGGRCTACARTCTACTTGTC
HIV.145 (SEQ ID NO:33)
 DGATWAYTTTTCCTTCYARATGTGTACAATCTA
HIV.146 (SEQ ID NO:34)
 CTATRTAKCCACTRGCYACATGRACTGCTACYA
HIV.147 (SEQ ID NO:35)
 CYTGYCCTGTYTCTGCTGGRATDACTTCTGCTT
HIV.149 (SEQ ID NO:36)
 TGSKGCCATTGTCTGTATGTAYTRYTKTTACTG
HIV.151 (SEQ ID NO:37)
 GAATKCCAAATTCCTGYTTRATHCCHGCCCACC
HIV.152 (SEQ ID NO:38)
 ATTCYAYTACYCCTTGACTTTGGGGRTTGTAGG
HIV.153 (SEQ ID NO:39)
 GBCCTATRATTTKCTTTAATTCHTTATTCATAG
HIV.154 (SEQ ID NO:40)
 CTSTCTTAAGRTGYTCAGCYTGMTCTCTTACYT
HIV.155 (SEQ ID NO:41)
 TAAAATTGTGRTRAAYACTGCCATTTGTACWG
HIV.156 (SEQ ID NO:42)
 CTGCACTGTAYCCCCCAATCCCCCYTYTTCTTT
HIV.157 (SEQ ID NO:43)
 TGTCTGTWGCTATYATRYCTAYTATTCTYTCCC
HIV.158 (SEQ ID NO:44)
 TTRTRATTTGYTTTTGTARTTCTYTARTTTGTA

HIV Capture Probes

HIV.103 (SEQ ID NO:45)
 CATCTGCTCCTGTRTCTAATAGAGCTTCYTTTA
HIV.111 (SEQ ID NO:46)
 ATCCATYCCTGGCTTTAATTTTACTGGTACAGT
HIV.118 (SEQ ID NO:47)
 TATTCCTAAYTGRACTTCCCARAARTCYTGAGT
HIV.119 (SEQ ID NO:48)
 ACWYTGGAATATYGCYGGTGATCCTTTCCAYCC
HIV.126 (SEQ ID NO:49)
 CCATTTRTCAGGRTGGAGTTCATAMCCCATCCA
HIV.127 (SEQ ID NO:50)
 CTAYTATGGGKTCYKTYTCTAACTGGTACCAYA
HIV.134 (SEQ ID NO:51)
 ATCTGGTTGTGCTTGAATRATYCCYARTGCATA

HIV.143 (SEQ ID NO:52)
 CATGCATGGCTTCYCCTTTTAGYTGRCATTTAT
HIV.150 (SEQ ID NO:53)
 AACAGGCDGCYTTAACYGYAGYACTGGTGAAAT
HIV.159 (SEQ ID NO:54)
 TGTCYCTGTAATAAACCCGAAAATTTTGAATTT

Each amplifier probe contained, in addition to the sequences substantially complementary to the HIV sequences, the following 5' extension complementary to a segment of the amplifier multimer,

AGGCATAGGACCCGTGTCTT (SEQ ID NO:55).

Each capture probe contained, in addition to the sequences substantially complementary to HIV DNA, the following downstream sequence complementary to DNA bound to the solid phase (XT1*),

CTTCTTTGGAGAAAGTGGTG (SEQ ID NO:56).

In addition to the amplifier and capture probes, the following set of HIV spacer oligonucleotides was included in the hybridization mixture.

HIV Spacer Oligonucleotides

HIV.NOX107 (SEQ ID NO:57)
 TATAGCTTTHTDTCCRCAGATTTCTAYRR,
HIV.NOX109 (SEQ ID NO:58)
 VCCAAKCTGRGTCAACADATTTCKTCCRATTAT,
HIV.NOX124 (SEQ ID NO:59)
 TGGTGTGGTAARYCCCCACYTYAAYAGATGYYS,
HIV.NOX129 (SEQ ID NO:60)
 TCCTGCTTTTCCYWDTYTAGTYTCYCTRY,
HIV.NOX131 (SEQ ID NO:61)
 YTCAGTYTTCTGATTTGTYGTDTBHKTNADRGD,
HIV.NOX140 (SEQ ID NO:62)
 AATTRYTGTGATATTTYTCATGDTCHTCTTGRGCCTT,
HIV.NOX148 (SEQ ID NO:63)
 GCCATCTKCCTGCTAATTT-TARDAKRAARTATGCTGTYT.

Microtiter plates were prepared as follows. White Microlite 1 Removawell strips (polystyrene microtiter plates, 96 wells/plate) were purchased from Dynatech Inc. Each well was filled with 200 µl 1 N HCl and incubated at room temperature for 15–20 min. The plates were then washed 4 times with 1× PBS and the wells aspirated to remove liquid. The wells were then filled with 200 µl 1 N NaOH and incubated at room temperature for 15–20 min. The plates were again washed 4 times with 1× PBS and the wells aspirated to remove liquid.

Poly(phe-lys) was purchased from Sigma Chemicals, Inc. This polypeptide has a 1:1 molar ratio of phe:lys and an average m.w. of 47,900 gm/mole. It has an average length of 309 amino acids and contains 155 amines/mole. A 1 mg/ml solution of the polypeptide was mixed with 2M NaCl/1× PBS to a final concentration of 0.1 mg/ml (pH 6.0). 200 µL of this solution was added to each well. The plate was wrapped in plastic to prevent drying and incubated at 30° C. overnight. The plate was then washed 4 times with 1× PBS and the wells aspirated to remove liquid.

The following procedure was used to couple the oligonucleotide XT1* to the plates. Synthesis of XT1* was described in EPA 883096976. 20 mg disuccinimidyl suberate was dissolved in 300 µl dimethyl formamide (DMF). 26 $OD_{260}$ units of XT1* was added to 100 µl coupling buffer (50 mM sodium phosphate, pH 7.8). The coupling mixture was then added to the DSS-DMF solution and stirred with a magnetic stirrer for 30 min. An NAP-25 column was equilibrated with 10 mM sodium phosphate, pH 6.5. The coupling mixture DSS-DMF solution was added to 2 ml 10 M sodium phosphate, pH 6.5, at 4° C. The mixture was vortexed to mix and loaded onto the equilibrated NAP-25 column. DSS-activated XT1* DNA was eluted from the column with 3.5 ml 10 mM sodium phosphate, pH 6.5. 5.6 $OD_{260}$ units of eluted DSS-activated XT1* DNA was added to 1500 ml 50 mM sodium phosphate, pH 7.8. 50 µl of this solution was added to each well and the plates were incubated overnight. The plate was then washed 4 times with 1× PBS and the wells aspirated to remove liquid.

Final stripping of plates was accomplished as follows. 200 µL of 0.2N NaOH containing 0.5% (w/v) SDS was added to each well. The plate was wrapped in plastic and incubated at 650° C. for 60 min. The plate was then washed 4 times with 1× PBS and the wells aspirated to remove liquid. The stripped plate was stored with desiccant beads at 2–8° C.

A standard curve of HIV DNA was prepared by diluting cloned HIV DNA in HIV negative human serum and delivering aliquots of dilutions corresponding to a range of 10 to 200 tmoles (1 tmole=602 molecules or $10^{21}$ moles) to wells of microtiter dishes prepared as described above.

Sample preparation consisted of delivering 12.5 µl P-K Buffer (2 mg/ml proteinase K in 10 mM Tris-HCl, pH 8.0/0.15 M NaCl/10 mM EDTA, pH 8.0/1%SDS/40 µg/ml sonicated salmon sperm DNA) to each well. Plates were covered and agitated to mix samples, incubated at 65° C. to release nucleic acids, and then cooled on the benchtop for 5 min.

A cocktail of the HIV-specific amplifier and capture probes listed above was added to each well (50 fmoles capture probes, 50 fmoles amplifier probes/well). Plates were covered and gently agitated to mix reagents and then incubated at 65° C. for 30 min.

Neutralization buffer was then added to each well (0.77 M 3-(N-morpholino)propane sulfonic acid/1.845 M NaCl/ 0.185 M sodium citrate). Plates were covered and incubated for 12–18 hr at 65° C.

The contents of each well were aspirated to remove all fluid, and the wells washed 2× with washing buffer (0.1% SDS/0.015 M NaCl/ 0.0015 M sodium citrate).

The amplifier multimer was then added to each well (40 µl of 2.5 fmole/µl solution in 50% horse serum/0.06 M NaCl/0.06 M sodium citrate/0.1% SDS mixed 1:1 with 4× SSC/0.1% SDS/0.5% "blocking reagent" a purified fraction of dry milk powder, Boehringer Mannheim, catalog No. 1096 176). After covering plates and agitating to mix the contents in the wells, the plates were incubated for 15 min at 55° C.

After a further 5 min period at room temperature, the wells were washed as described above.

Alkaline phosphatase label probe, disclosed in EP 883096976, was then added to each well (40 µl/well of 2.5 fmoles/µl). After incubation at 55° C. for 15 min, and 5 min at room temperature, the wells were washed twice as above and then 3× with 0.015 M NaCl/0.0015 M sodium citrate.

An enzyme-triggered dioxetane (Schaap et al., Tet. Lett. (1987) 28:1159–1162 and EPA Pub. No. 0254051), obtained from Lumigen, Inc., was employed. 20 µl Lumiphos 530 (Lumigen) was added to each well. The wells were tapped lightly so that the reagent would fall to the bottom and gently swirled to distribute the reagent evenly over the bottom. The wells were covered and incubated at 37° C. for 40 min.

Plates were then read on a Dynatech ML 1000 luminometer. Output was given as the full integral of the light produced during the reaction.

Results are shown in the Table below. Results for each standard sample are expressed as the difference between the mean of the negative control plus two standard deviations and the mean of the sample minus two standard deviations (delta). If delta is greater than zero, the sample is considered positive.

Results from the standard curve of the HIV probes is shown in Table I. These results indicate the ability of these probe sets to detect 50 tmoles of the HIV DNA standard.

TABLE I

| Analyte HIV tmole/well | Delta |
|---|---|
| 0 | — |
| 10 | −0.56 |
| 20 | −0.51 |
| 50 | 0.39 |
| 100 | 1.93 |
| 200 | 5.48 |

Example 3

Detection of HIV Viral RNA

HIV RNA was detected using essentially the same procedure as above with the following modifications.

A standard curve of HIV RNA was prepared by serially diluting HIV virus stock in normal human serum to a range between 125 to 5000 $TCID_{50}$/ml ($TCID_{50}$ is the 50% tissue culture infectious dose endpoint). A proteinase K solution was prepared by adding 10 mg proteinase K to 5 ml HIV capture diluent (53 mM Tris-HCl, pH 8/ 10.6 mM EDTA/ 1.3% SDS/ 16 µg/ml sonicated salmon sperm DNA/ 5.3× SSC/ 1 mg/ml proteinase K) made 7% in formamide stored at −20° C. Equimolar mixtures of capture probes, label probes and spacer oligonucleotides were added to the prot:einase K solution such that the final concentration of each probe was 1670 fmoles/ml. After addition of 30 µl of the probe/proteinase K solution to each well of microtiter plates prepared as above, 10 µl of appropriate virus dilutions were added to each well. Plates were covered, shaken to mix and then incubated at 65° C. for 16 hr.

Plates were removed from the incubator and cooled on the bench top for 10 min. The wells were washed 2× as described in Example 2 above. The 15×3 multimer was diluted to 1 fmole/µl in Amp/Label diluent (prepared by mixing 2.22 ml DEPC-treated $H_2O$ (DEPC is diethylpyrocarbonate), 1.35 ml 10% SDS, 240 µl 1 M Tris pH 8.0, 20 µl horse serum, adjusted to 2 mg/ml in proteinase K and heated to 65° C. for 2 hr, then added to 240 µl of 0.1 M PMSF and heated at 37° C. for 1 hr, after which was added 4 ml DEPC-treated $H_2O$, 4 ml 10% SDS and 8 ml 20× SSC). The diluted 15×3 multimer was added at 40 µl/well, the plates sealed, shaken, and incubated at 55° C. for 30 min.

The plates were then cooled at room temperature for 10 minutes, and washed as described above. Alkaline phosphatase label probe was diluted to 2.5 fmoles/µl in Amp/ Label diluent and 40 µl added to each well. Plates were covered, shaken, and incubated at 55° C. for 15 min.

Plates were cooled 10 min at room temperature, washed 2× as above and then 3× with 0.15 M NaCl/0.015 M sodium citrate. Substrate was added and luminescence measured as above. Sensitivity of the assay was about 1.25 $TCID_{50}$, as shown in the Table below.

TABLE II

| TCID$_{50}$ | delta |
|---|---|
| 0.00 | — |
| 1.25 | 0.11 |
| 2.50 | 2.60 |
| 5.00 | 6.37 |
| 10.00 | 14.10 |
| 50.00 | 90.70 |

Example 4

Comparison of Clustered vs Interspersed Probe Sets

HIV RNA was detected using essentially the same procedure as in Example 3, except for the following modifications. The RNA standard was prepared by transcription of a 9.0 KB HIV transcript from plasmid pBHBK10S (Chang, P.S., et al., *Clin. Biotech.* 2:23, 1990) using T7 RNA polymerase. This HIV RNA was quantitated by hybridization with gag and pol probes captured by HAP chromatography. The RNA standard was serially diluted in the proteinase K diluent described above to a range between 2.5 to 100 atomoles per ml, and the equimolar mixtures of capture probes, label probes, and spacer oligonucleotides were added such that the concentration of each probe was 1670 fmoles/ml. Two arrangements of capture and label probes were tested: scattered capture probes, such that capture probes are interspersed with label probes, and clustered capture probes, such that the capture probes are arranged in contiguous clusters with respect to label probes. The clustered probe sets are shown below.

CLUSTERED HIV CAPTURE PROBES

HIV.116 (SEQ ID NO:14)
  TCTCCAYTTRGTRCTGTCYTTTTTCTTTATRGC
HIV.117 (SEQ ID NO:15)
  TYTYYTATTAAGYTCYCTGAAATCTACTARTTT
HIV.118 (SEQ ID NO:47)
  TATTCCTAAYTGRACTTCCCARAARTCYTGAGT
HIV.119 (SEQ ID NO:48)
  ACWYTGGAATATYGCYGGTGATCCTTTCCAYCC
HIV.120 (SEQ ID NO:16)
  TKTTYTAAARGGYTCYAAGATTTTTGTCATRCT
HIV.155 (SEQ ID NO:41)
  TAAAATTGTGRATRAAYACTGCCATTTGTACWG
HIV.156 (SEQ ID NO:42)
  CTGCACTGTAYCCCCCAATCCCCCYTYTTCTTT
HIV.157 (SEQ ID NO:43)
  TGTCTGTWGCTATYATRYCTAYTATTCTYTCCC
HIV.158 (SEQ ID NO:44)
  TTRTRATTTGYTTTTGTARTTCTYTARTTTGTA
HIV.159 (SEQ ID NO:54)
  TGTCYCTGTAATAAACCCGAAAATTTTGAATTT

CLUSTERED HIV AMPLIFIER PROBES

HIV.103 (SEQ ID NO:45)
  CATCTGCTCCTGTRTCTAATAGAGCTTCYTTTA
HIV.104 (SEQ ID NO:5)
  TTCCTGGCAAAYYYATKTCTYCTAMTACTGTAT
HIV.105 (SEQ ID NO:6)
  CTCCAATTCCYCCTATCATTTTTGGYTTCCATY
HIV.106 (SEQ ID NO:7)
  KTATYTGATCRTAYTGTCYYACTTTGATAAAAC
HIV.108 (SEQ ID NO:8)
  GTTGACAGGYGTAGGTCCTACYAATAYTGTACC
HIV.110 (SEQ ID NO:9)
  YTCAATAGGRCTAATKGGRAAATTTAAAGTRCA
HIV.111 (SEQ ID NO:46)
  ATCCATYCCTGGCTTTAATTTTACTGGTACAGT
HIV.112 (SEQ ID NO:10)
  YTCTGTCAATGGCCATTGYTTRACYYTTGGGCC
HIV.113 (SEQ ID NO:11)
  TKTACAWATYTCTRYTAATGCTTTTATTTTYTC
HIV.114 (SEQ ID NO:12)
  AAYTYTTGAAATYTTYCCTTCCTTTTCCATHTC
HIV.115 (SEQ ID NO:13)
  AAATAYKGGAGTATTRTATGGATTYTCAGGCCC
HIV.121 (SEQ ID NO:17)
  CATGTATTGATADATRAYYATKTCTGGATTTTG
HIV.122 (SEQ ID NO:18)
  TATYTCTAARTCAGAYCCTACATACAAATCATC
HIV.123 (SEQ ID NO:19)
  TCTYARYTCCTCTATTTTTGYTCTATGCTGYYC
HIV.125 (SEQ ID NO:20)
  AAGRAATGGRGGTTCTTTCTGATGYTTYTTRTC
HIV.126 (SEQ ID NO:49)
  CCATTTRTCAGGRTGGAGTTCATAMCCCATCCA
HIV.127 (SEQ ID NO:50)
  CTAYTATGGGKTCYKTYTCTAACTGGTACCAYA
HIV.128 (SEQ ID NO:21)
  TRGCTGCYCCATCTACATAGAAVGTTTCTGCWC
HIV.130 (SEQ ID NO:22)
  GACAACYTTYTGTCTTCCAYTGTYAGTWASATA
HIV.132 (SEQ ID NO:23)
  YGAATCCTGYAAVGCTARRTDAATTGCTTGTAA
HIV.133 (SEQ ID NO:24)
  YTGTGARTCTGTYACTATRTTTACTTCTRRTCC
HIV.134 (SEQ ID NO:51)
  ATCTGGTTGTGTTGAATRATYCCYARTGCATA
HIV.135 (SEQ ID NO:25)
  TATTATTTGAYTRACWAWCTCTGATTCACTYTK
HIV.136 (SEQ ID NO:26)
  CAGRTARACYTTTTCCTTTTTATTARYTGYTC
HIV.137 (SEQ ID NO:27)
  TCCTCCAATYCCTTTRTGTGCTGGTACCCATGM
HIV.138 (SEQ ID NO:28)
  TCCHBBACTGACTAATYTATCTACTTGTTCATT
HIV.139 (SEQ ID NO:29)
  ATCTATTCCATYYAAAAATAGYAYYTTYCTGAT
HIV.141 (SEQ ID NO:30)
  GTGGYAGRTTAAARTCAYTAGCCATTGCTYTCC
HIV.142 (SEQ ID NO:31)
  CACAGCTRGCTACTATTTCYTTYGCTACYAYRG
HIV.143 (SEQ ID NO:52)
  CATGCATGGCTTCYCCTTTTAGYTGRCATTTAT
HIV.144 (SEQ ID NO:32)
  RYTGCCATATYCCKGGRCTACARTCTACTTGTC
HIV.145 (SEQ ID NO:33)
  DGATWAYTTTTCCTTCYARATGTGTACAATCTA
HIV.146 (SEQ ID NO:34)
  CTATRTAKCCACTRGCYACATGRACTGCTACYA
HIV.147 (SEQ ID NO:35)
  CYTGYCCTGTYTCTGCTGGRATDACTTCTGCTT

HIV.149 (SEQ ID NO:36)
TGSKGCCATTGTCTGTATGTAYTRYTKTTACTG
HIV.150 (SEQ ID NO:53)
AACAGGCDGCYTTAACYGYAGYACTGGTGAAAT
HIV.151 (SEQ ID NO:37)
GAATKCCAAATTCCTGYTTRATHCCHGCCCACC
HIV.152 (SEQ ID NO:38)
ATTCYAYTACYCCTTGACTTTGGGGRTTGTAGG
HIV.153 (SEQ ID NO:39)
GBCCTATRATTTKCTTTAATTCHTTATTCATAG
HIV.154 (SEQ ID NO:40)
CTSTCTTAAGRTGYTCAGCYTGMTCTCTTACYT

After addition of 30 μl of the analyte/probe/proteinase K solution to each well, 10 μl of normal human serum was added and the assay carried out as described in Example 3. As shown in Table III, the sensitivity of the assay with scattered versus the clustered capture arrangement was similar. Using the clustered capture extenders sensitivity was 50 to 100 tmoles, whereas using the scattered capture extenders, sensitivity was 100 to 500 tmoles.

TABLE 3

| Probe Arrangement | Analyte tmoles | Delta |
|---|---|---|
| Clustered | 0 | — |
|  | 25 | −0.16 |
|  | 50 | 0.36 |
|  | 100 | 0.65 |
|  | 500 | 4.45 |
|  | 1000 | 6.24 |
| Scattered | 0 | — |
|  | 25 | −0.24 |
|  | 50 | 0.25 |
|  | 100 | −0.11 |
|  | 500 | 2.52 |
|  | 1000 | 4.79 |

Modifications of the above-described modes for carrying out the invention that are obvious to those of skill in biochemistry, nucleic acid hybridization assays, and related fields are intended to be within the scope of the following claims.

What is claimed is:

1. A synthetic oligonucleotide useful as an amplifier probe in a sandwich hybridization assay for HIV, wherein said oligonucleotide consists of;
- a first segment having a minimum length of 33 nucleotides and a maximum length of about 100 nucleotides which segment is at least 90% homologous to a segment of HIV nucleic acid, wherein said first segment comprises a nucleotide sequence selected from the group consisting of SEQ ID NOS: 5–13, 17–40, 45, 46, and 49–53; and
- a second segment consisting of a nucleotide sequence which is at least 90% homologous to an oligonucleotide segment of a nucleic acid multimer wherein said second segment is not complementary to HIV nucleic acid;

and optionally one or more noncomplementary segments each consisting of a nucleotide sequence that is not complementary to HIV nucleic acid.

2. The synthetic oligonucleotide of claim 1, wherein said second segment comprises SEQ ID NO:55.

3. The synthetic oligonucleotide of claim 1, wherein said first segment consists of a nucleotide sequence selected from the group consisting of SEQ ID NOS: 5–13, 17–40, 45, 46, and 49–53.

4. A synthetic oligonucleotide useful as a capture probe in a sandwich hybridization assay for HIV, wherein the synthetic oligonucleotide consists of:

a first segment having a minimum length of 33 nucleotides and a maximum length of about 100 nucleotides which segment is at least 90% homologous to a segment of HIV nucleic acid, wherein said first segment comprises a nucleotide sequence selected from the group consisting of SEQ ID NOS: 14–16, 41–44, 47, 48 and 54; and a second segment consisting of a nucleotide sequence which is at least 90% homologous to an oligonucleotide bound to a solid phase wherein said second segment is not complementary to HIV nucleic acid;

and optionally one or more noncomplementary segments each consisting of a nucleotide sequence that is not complementary to HIV nucleic acid.

5. The synthetic oligonucleotide of claim 4, wherein said second segment comprises SEQ ID NO: 56.

6. The synthetic oligonucleotide of claim 4, wherein said first segment consists of a nucleotide sequence selected from the group consisting of SEQ ID NOS: 14–16, 41–44, 47, 48 and 54.

7. A set of synthetic oligonucleotides useful as amplifier probes in a sandwich hybridization assay for HIV, comprising at least two different oligonucleotide probes, wherein each oligonucleotide probe consists of:

a first segment having a minimum length of 33 nucleotides and a maximum length of about 100 nucleotides which segment is at least 90% homologous to a segment of HIV nucleic acid, wherein said first segment comprises a nucleotide sequence selected from the group consisting of SEQ ID NOS: 5–13, 17–40, 45, 46 and 49–53; and a second segment consisting of a nucleotide sequence which is at least 90% homologous to an oligonucleotide segment of a nucleic acid multimer wherein said second segment is not complementary to HIV nucleic acid;

and optionally one or more noncomplementary segments each consisting of a nucleotide sequence that is not complementary to HIV nucleic acid.

8. The set of synthetic oligonucleotides of claim 7, wherein each said second segment comprises SEQ ID NO: 55.

9. The set of synthetic oligonucleotides of claim 7, wherein said set comprises at least five different oligonucleotide probes.

10. The set of synthetic oligonucleotides of claim 7, wherein each of said first segments consists of a nucleotide sequence selected from the group consisting of SEQ ID NOS: 5–13, 17–40, 45, 46 and 49–53.

11. A set of synthetic oligonucleotides useful as capture probes in a sandwich hybridization assay for HIV, comprising at least two different oligonucleotide probes, wherein each oligonucleotide probe consists of:

a first segment having a minimum length of about 25 nucleotides and a maximum length of about 100 nucleotides which segment is at least 90% homologous to a segment of HIV nucleic acid, wherein said first segment comprises a nucleotide sequence selected from the group consisting of SEQ ID NOS: 14–16, 41–44, 47, 48 and 54; and a second segment consisting of a nucleotide sequence which is at least 90% homologous to an oligonucleotide bound to a solid phase wherein said second segment is not complementary to HIV nucleic acid;

and optionally one or more noncomplementary segments each consisting of a nucleotide sequence that is not complementary to HIV nucleic acid.

12. The set of synthetic oligonucleotides of claim 11, wherein each said second segment comprises SEQ ID NO; 56.

13. The set of synthetic oligonucleotides of claim 11, wherein said set comprises at least five different oligonucleotide probes.

14. The set of synthetic oligonucleotides of claim 11, wherein each of said first segments consists of a nucleotide sequence selected from the group consisting of SEQ ID NOS: 14–16, 41–44, 47, 48 and 54.

15. A solution sandwich hybridization assay for detecting the presence of HIV in a sample, comprising (a) contacting the sample with (i) amplifier probes comprising the set of synthetic oligonucleotides of claim 7 and (ii) a set of capture probe oligonucleotides wherein there is a molar excess of amplifier probes and of capture probes over analyte nucleic acid in the sample, wherein said set of capture probe oligonucleotides comprises at least two different oligonucleotides each of which consists of a first segment having a minimum length of 33 nucleotides and a maximum length of about 10.0 nucleotides which segment is at least 90% homologous to a segment of HIV nucleic acid, wherein said first segment comprises a nucleotide sequence selected from the group consisting of SEQ ID NOS: 14–16, 41–44, 47, 48 and 54; and a second segment consisting of a nucleotide sequence which is at least 90% homologous to an oligonucleotide bound to a solid phase wherein said second segment is not complementary to HIV nucleic acid;

and optionally one or more noncomplementary segments each consisting of a nucleotide sequence that is not complementary to HIV nucleic acid;

(b) contacting the product of step (a) with said oligonucleotide bound to the solid phase;

(c) thereafter separating materials not bound to the solid phase;

(d) contacting the bound product of step (c) with a nucleic acid multimer, said multimer comprising at least one oligonucleotide segment that is at least 90% homologous to the second segment of the amplifier probe polynucleotide and a multiplicity of second oligonucleotide segments that are at least 90% homologous to a labeled oligonucleotide;

(e) removing unbound multimer;

(f) contacting the solid phase complex product of step (e) with the labeled oligonucleotide;

(g) removing unbound labeled oligonucleotide; and (h) detecting the presence of label in the solid phase complex product of step (g) and, thereby, detecting the presence of virus in the sample.

16. The assay of claim 15, wherein said set of amplifier probes comprises at least five different oligonucleotide probes.

17. The assay of claim 15, wherein said set of capture probes comprises at least five different oligonucleotide probes.

18. A kit for the detection of HIV in a sample comprising in combination
  (i) a set of amplifier probe oligonucleotides comprising the set of oligonucleotides of claim 7;
  (ii) a set of capture probe oligonucleotides comprising at least two different oligonucleotides each of which consists of
    a first segment having a minimum length of 33 nucleotides and a maximum length of about 100 nucleotides which segment is at least 90% homologous to a segment of HIV nucleic acid, wherein said first segment comprises a nucleotide sequence selected from the group consisting of SEQ ID NOS: 14–16, 41–44, 47, 48 and 54; and
    a second segment consisting of a nucleotide sequence which is at least 90% homologous to an oligonucleolide bound to a solid phase wherein said second segment is not complementary to HIV nucleic acid; and optionally one or more noncomplementary segments each consisting of a nucleotide sequence that is not complementary to HIV nucleic acid;
  (iii) a nucleic acid multimer, said multimer comprising at least one oligonucleotide segment that is at least 90% homologous to the second segment of the amplifier probe polynucleotide and a multiplicity of second oligonucleotide segments that are at least 90% homologous to a labeled oligonucleotide; and
  (iv) a labeled oligonucleotide.

19. The kit of claim 18, wherein said set of amplifier probes comprises at least five different oligonucleotide probes.

20. The kit of claim 18, wherein said set of capture probes comprises at least five different oligonucleotide probes.

* * * * *

SEQUENCE LISTING (1) GENERAL INFORMATION:

(iii) NUMBER OF SEQUENCES: 63

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (xi) SEQUENCE DESCRIPTION: SEQ ID NO:1:

CGTGGAGACA CGGGTCCTAT GCCT                                   24

(2) INFORMATION FOR SEQ ID NO:2:

(i) SEQUENCE CHARACTERISTICS:
      (A) LENGTH: 60 base pairs
      (B) TYPE: nucleic acid
      (C) STRANDEDNESS: single
      (D) TOPOLOGY: linear (xi) SEQUENCE DESCRIPTION: SEQ ID NO:2:

GATGTGGTTG TCGTACTTGA TGTGGTTGTC GTACTTGATG TGGTTGTCGT ACTTGCGTAG    60

(2) INFORMATION FOR SEQ ID NO:3:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (xi) SEQUENCE DESCRIPTION: SEQ ID NO:3:

TCCACGAAAA AAAAAA                                                   16

(2) INFORMATION FOR SEQ ID NO:4:

(i) SEQUENCE CHARACTERISTICS:
      (A) LENGTH: 12 base pairs (B) TYPE: nucleic acid
        (C) STRANDEDNESS: single
        (D) TOPOLOGY: linear (xi) SEQUENCE DESCRIPTION: SEQ ID NO:4:

CAGTCACTAC GC                                                              12

(2) INFORMATION FOR SEQ ID NO:5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:5:

TTCCTGGCAA AYYYATKTCT YCTAMTACTG TAT                                        33

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:6:

CTCCAATTCC YCCTATCATT TTTGGYTTCC ATY                                        33

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:7:

KTATYTGATC RTAYTGTCYY ACTTTGATAA AAC                                        33

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:8:

GTTGACAGGY GTAGGTCCTA CYAATAYTGT ACC                                        33

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:9:

YTCAATAGGR CTAATKGGRA AATTTAAAGT RCA                                        33

(2) INFORMATION FOR SEQ ID NO:10:

(i) SEQUENCE CHARACTERISTICS:
        (A) LENGTH: 33 base pairs
        (B) TYPE: nucleic acid (C) STRANDEDNESS: single
         (D) TOPOLOGY: linear (xi) SEQUENCE DESCRIPTION: SEQ ID NO:10:

YTCTGTCAAT GGCCATTGYT TRACYYTTGG GCC					33

(2) INFORMATION FOR SEQ ID NO:11:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (xi) SEQUENCE DESCRIPTION: SEQ ID NO:11:

TKTACAWATY TCTRYTAATG CTTTTATTTT YTC					33

(2) INFORMATION FOR SEQ ID NO:12:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (xi) SEQUENCE DESCRIPTION: SEQ ID NO:12:

AAYTYTTGAA ATYTTYCCTT CCTTTTCCAT HTC					33

(2) INFORMATION FOR SEQ ID NO:13:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (xi) SEQUENCE DESCRIPTION: SEQ ID NO:13:

AAATAYKGGA GTATTRTATG GATTYTCAGG CCC					33

(2) INFORMATION FOR SEQ ID NO:14:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (xi) SEQUENCE DESCRIPTION: SEQ ID NO:14:

TCTCCAYTTR GTRCTGTCYT TTTTCTTTAT RGC					33

(2) INFORMATION FOR SEQ ID NO:15:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (xi) SEQUENCE DESCRIPTION: SEQ ID NO:15:

TYTYYTATTA AGYTCYCTGA AATCTACTAR TTT					33

(2) INFORMATION FOR SEQ ID NO:16:

(i) SEQUENCE CHARACTERISTICS:
         (A) LENGTH: 33 base pairs
         (B) TYPE: nucleic acid
         (C) STRANDEDNESS: single (D) TOPOLOGY: linear (xi) SEQUENCE DESCRIPTION: SEQ ID NO:16:

TKTTYTAAAR GGYTCYAAGA TTTTTGTCAT RCT                               33

(2) INFORMATION FOR SEQ ID NO:17:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:17:

CATGTATTGA TADATRAYYA TKTCTGGATT TTG                               33

(2) INFORMATION FOR SEQ ID NO:18:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:18:

TATYTCTAAR TCAGAYCCTA CATACAAATC ATC                               33

(2) INFORMATION FOR SEQ ID NO:19:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:19:

TCTYARYTCC TCTATTTTTG YTCTATGCTG YYC                               33

(2) INFORMATION FOR SEQ ID NO:20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:20:

AAGRAATGGR GGTTCTTTCT GATGYTTYTT RTC                              33

(2) INFORMATION FOR SEQ ID NO:21:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:21:

TRGCTGCYCC ATCTACATAG AAVGTTTCTG CWC                              33

(2) INFORMATION FOR SEQ ID NO:22:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:22:

GACAACYTTY TGTCTTCCAY TGTYAGTWAS ATA                                                33

(2) INFORMATION FOR SEQ ID NO:23:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:23:

YGAATCCTGY AAVGCTARRT DAATTGCTTG TAA                                                33

(2) INFORMATION FOR SEQ ID NO:24:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:24:

YTGTGARTCT GTYACTATRT TTACTTCTRR TCC                                                33

(2) INFORMATION FOR SEQ ID NO:25:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:25:

TATTATTTGA YTRACWAWCT CTGATTCACT YTK                                                33

(2) INFORMATION FOR SEQ ID NO:26:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:26:

CAGRTARACY TTTTCCTTTT TTATTARYTG YTC                                                33

(2) INFORMATION FOR SEQ ID NO:27:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:27:

TCCTCCAATY CCTTTRTGTG CTGGTACCCA TGM                                                33

(2) INFORMATION FOR SEQ ID NO:28:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:28:

TCCHBBACTG ACTAATYTAT CTACTTGTTC ATT                33

(2) INFORMATION FOR SEQ ID NO:29:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:29:

ATCTATTCCA TYYAAAAATA GYAYYTTYCT GAT                33

(2) INFORMATION FOR SEQ ID NO:30:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:30:

GTGGYAGRTT AAAARTCAYTA GCCATTGCTY TCC               33

(2) INFORMATION FOR SEQ ID NO:31:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:31:

CACAGCTRGC TACTATTTCY TTYGCTACYA YRG                33

(2) INFORMATION FOR SEQ ID NO:32:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:32:

RYTGCCATAT YCCKGGRCTA CARTCTACTT GTC                33

(2) INFORMATION FOR SEQ ID NO:33:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:33:

DGATWAYTTT TCCTTCYARA TGTGTACAAT CTA                33

(2) INFORMATION FOR SEQ ID NO:34:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:34:

CTATRTAKCC ACTRGCYACA TGRACTGCTA CYA                                33

(2) INFORMATION FOR SEQ ID NO:35:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:35:

CYTGYCCTGT YTCTGCTGGR ATDACTTCTG CTT                                33

(2) INFORMATION FOR SEQ ID NO:36:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:36:

TGSKGCCATT GTCTGTATGT AYTRYTKTTA CTG                                33

(2) INFORMATION FOR SEQ ID NO:37:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:37:

GAATKCCAAA TTCCTGYTTR ATHCCHGCCC ACC                                33

(2) INFORMATION FOR SEQ ID NO:38:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:38:

ATTCYAYTAC YCCTTGACTT TGGGGRTTGT AGG                                33

(2) INFORMATION FOR SEQ ID NO:39:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:39:

GBCCTATRAT TTKCTTTAAT TCHTTATTCA TAG                                33

(2) INFORMATION FOR SEQ ID NO:40:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:40:

CTSTCTTAAG RTGYTCAGCY TGMTCTCTTA CYT                                33

(2) INFORMATION FOR SEQ ID NO:41:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:41:

TAAAATTGTG RATRAAYACT GCCATTTGTA CWG                                33

(2) INFORMATION FOR SEQ ID NO:42:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:42:

CTGCACTGTA YCCCCCAATC CCCCYTYTTC TTT                                33

(2) INFORMATION FOR SEQ ID NO:43:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:43:

TGTCTGTWGC TATYATRYCT AYTATTCTYT CCC                                33

(2) INFORMATION FOR SEQ ID NO:44:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:44:

TTRTRATTTG YTTTTGTART TCTYTARTTT GTA                                33

(2) INFORMATION FOR SEQ ID NO:45:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:45:

CATCTGCTCC TGTRTCTAAT AGAGCTTCYT TTA                                33

(2) INFORMATION FOR SEQ ID NO:46:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:46:

ATCCATYCCT GGCTTTAATT TTACTGGTAC AGT                                33

(2) INFORMATION FOR SEQ ID NO:47:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:47:

TATTCCTAAY TGRACTTCCC ARAARTCYTG AGT                            33

(2) INFORMATION FOR SEQ ID NO:48:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:48:

ACWYTGGAAT ATYGCYGGTG ATCCTTTCCA YCC                            33

(2) INFORMATION FOR SEQ ID NO:49:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:49:

CCATTTRTCA GGRTGGAGTT CATAMCCCAT CCA                            33

(2) INFORMATION FOR SEQ ID NO:50:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:50:

CTAYTATGGG KTCYKTYTCT AACTGGTACC AYA                            33

(2) INFORMATION FOR SEQ ID NO:51:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:51:

ATCTGGTTGT GCTTGAATRA TYCCYARTGC ATA                            33

(2) INFORMATION FOR SEQ ID NO:52:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:52:

CATGCATGGC TTCYCCTTTT AGYTGRCATT TAT                            33

(2) INFORMATION FOR SEQ ID NO:53:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:53:

```
AACAGGCDGC YTTAACYGYA GYACTGGTGA AAT                              33
```

(2) INFORMATION FOR SEQ ID NO:54:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:54:

```
TGTCYCTGTA ATAAACCCGA AAATTTTGAA TTT                              33
```

(2) INFORMATION FOR SEQ ID NO:55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:55:

```
AGGCATAGGA CCCGTGTCTT                                             20
```

(2) INFORMATION FOR SEQ ID NO:56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:56:

```
CTTCTTTGGA GAAAGTGGTG                                             20
```

(2) INFORMATION FOR SEQ ID NO:57:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:57:

```
TATAGCTTTH TDTCCRCAGA TTTCTAYRR                                   29
```

(2) INFORMATION FOR SEQ ID NO:58:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:58:

```
VCCAAKCTGR GTCAACADAT TTCKTCCRAT TAT                              33
```

-continued (2) INFORMATION FOR SEQ ID NO:59:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:59:

TGGTGTGGTA ARYCCCCACY TYAAYAGATG YYS    33

(2) INFORMATION FOR SEQ ID NO:60:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:60:

TCCTGCTTTT CCYWDTYTAG TYTCYCTRY    29

(2) INFORMATION FOR SEQ ID NO:61:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:61:

YTCAGTYTTC TGATTTGTYG TDTBHKTNAD RGD    33

(2) INFORMATION FOR SEQ ID NO:62:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:62:

AATTRYTGTG ATATTTYTCA TGDTCHTCTT GRGCCTT    37

(2) INFORMATION FOR SEQ ID NO:63:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:63:

GCCATCTKCC TGCTAATTTT ARDAKRAART ATGCTGTYT    39